United States Patent
Hauger et al.

(10) Patent No.: US 8,929,974 B2
(45) Date of Patent: Jan. 6, 2015

(54) SYSTEM AND METHOD FOR EXAMINING AN ILLUMINATED OBJECT

(75) Inventors: Christoph Hauger, Aalen (DE); Werner Nahm, Buhlerzell (DE); Theo Lasser, Denges (CH); Marcel Leutenegger, Silenen (CH); Erica Martin-Williams, Pully (CH); Antonio Lopez, Renens (CH)

(73) Assignee: Carl Zeiss Meditec AG, Jena (DE)

( * ) Notice: Subject to any disclaimer, the term of this patent is extended or adjusted under 35 U.S.C. 154(b) by 1309 days.

(21) Appl. No.: 12/757,000

(22) Filed: Apr. 8, 2010

(65) Prior Publication Data

US 2011/0090325 A1    Apr. 21, 2011

Related U.S. Application Data

(63) Continuation-in-part of application No. PCT/EP2008/008547, filed on Oct. 9, 2008.

(30) Foreign Application Priority Data

Oct. 9, 2007   (DE) .......................... 10 2007 048 362

(51) Int. Cl.
*A61B 6/00*      (2006.01)
*G01N 21/64*    (2006.01)
(Continued)

(52) U.S. Cl.
CPC .......... *G01N 21/6408* (2013.01); *A61B 5/0261* (2013.01); *A61B 5/14546* (2013.01);
(Continued)

(58) Field of Classification Search
CPC .... A61B 5/0059; A61B 6/5217; A61B 6/507; A61B 5/0042; A61B 2018/00446; A61B 2576/026; A61B 5/0261; A61B 5/14553; G06T 7/0012; G06T 2207/30016
See application file for complete search history.

(56) References Cited

U.S. PATENT DOCUMENTS 4,109,647 A    8/1978   Stern et al.
5,361,769 A   11/1994   Nilsson
(Continued)

FOREIGN PATENT DOCUMENTS

AT       409 451 B      8/2002
DE    697 27 220 T2   12/2004
(Continued)

OTHER PUBLICATIONS

Leithner, "Untersuchung der Sauerstoffkonzentrationsveränderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/dissertationen/leithner-christoph-2003-07-14/> [English Abstract and Machine Translation], 4 pages total.

(Continued)

*Primary Examiner* — Unsu Jung
*Assistant Examiner* — Amanda Lauritzen Moher
(74) *Attorney, Agent, or Firm* — Patent Portfolio Builders PLLC

(57) ABSTRACT

In a system and a method for examining an object containing a fluid liquid, the object is illuminated with measuring light and images are temporarily shortly subsequently recorded. The images are evaluated per pixel to determine perfusion data from a high frequency portion above 1 kHz and to determine further information about properties of the object from a low frequency portion below 100 Hz, such as a degree of oxygenation of hemoglobin, a concentration of hemoglobin or a concentration of ICG. This information determined by evaluation is displayed in a form of an image in superposition with a white light image of the object.

20 Claims, 12 Drawing Sheets

(51) Int. Cl.
  *A61B 5/026* (2006.01)
  *A61B 5/145* (2006.01)
  *A61B 5/1455* (2006.01)
  *G01N 21/47* (2006.01)
  *G06T 7/00* (2006.01)
  *A61B 18/00* (2006.01)
  *A61B 5/00* (2006.01)

(52) U.S. Cl.
  CPC .......... *A61B 5/1455* (2013.01); *G01N 21/4795* (2013.01); *G01N 21/6428* (2013.01); *G01N 21/6456* (2013.01); *G06T 7/0012* (2013.01); *A61B 2576/026* (2013.01); *A61B 2018/00446* (2013.01); *G06T 2207/30016* (2013.01); *A61B 5/14553* (2013.01); *A61B 5/0042* (2013.01); *G01N 2021/6482* (2013.01)
  USPC ........... 600/477; 600/363; 600/479; 600/504; 382/128

(56) References Cited

U.S. PATENT DOCUMENTS

| | | | |
|---|---|---|---|
| 6,263,227 | B1 | 7/2001 | Boggett et al. |
| 8,480,579 | B2 * | 7/2013 | Serov et al. .................. 600/363 |
| 2003/0050543 | A1 | 3/2003 | Hartmann |
| 2004/0109231 | A1 * | 6/2004 | Haisch et al. ................ 359/385 |
| 2005/0187477 | A1 | 8/2005 | Serov et al. |
| 2005/0254008 | A1 | 11/2005 | Ferguson et al. |
| 2008/0007733 | A1 * | 1/2008 | Marks et al. .................. 356/477 |
| 2009/0054788 | A1 * | 2/2009 | Hauger et al. ................ 600/476 |
| 2009/0118623 | A1 * | 5/2009 | Serov et al. .................. 600/476 |
| 2011/0013002 | A1 * | 1/2011 | Thompson et al. ............ 348/77 |
| 2013/0296715 | A1 * | 11/2013 | Lasser et al. ................. 600/479 |

FOREIGN PATENT DOCUMENTS

| | | | |
|---|---|---|---|
| EP | 1 874 181 A1 | | 1/2008 |
| WO | WO 2006/111836 | * | 10/2006 |
| WO | WO 2006/111836 A1 | | 10/2006 |
| WO | WO 2006/111909 A1 | | 10/2006 |

OTHER PUBLICATIONS

Patent Application No. PCT/IB2005/051289, filed Apr. 20, 2005, unpublished; priority application of WO Publication 2006/111836.

Raabe et al., "See the Brain at Work—Intraoperative Laser Doppler Functional Brain Imaging", NeuroImage, 2009; 44, 2009:1284-1289.

Sheth et al., "Linear and nonlinear relationships between neuronal activity, oxygen metabolism, and hemodynamic responses", Neuron, Apr. 22, 2004; 42(2):347-355.

Stern, "In vivo evaluation of microcirculation by coherent light scattering", Nature, Mar. 6, 1975; 254:56-58.

Draijer et al., "Laser Doppler Perfusion Imaging with a High-Speed CMOS-Camera," Proceedings of SPIE-OSA Biomedical Optics-Novel Optical Instrumentation for Biomedical Applications III, Jun. 17, 2007, 7 pages, vol. 6631, Copyright 2007, SPIE-OSA.

Serov et al., "Laser Doppler Perfusion Imaging with a Complimentary Metal Oxide Semiconductor Image Sensor," Optics Letters, Mar. 1, 2002, pp. 300-302, vol. 27, No. 5, Copyright 2002, Optical Society of America.

Serov et al., "Quasi-Parallel Laser Doppler Perfusion Imaging Using a CMOS Image Sensor," Proceeding of SPIE, 2003, pp. 73-84, vol. 5067, Copyright 2003, SPIE.

International Search Report for Application No. PCT/EP2008/008547, mailed on Jun. 2, 2009; 6 pages.

Written Opinion for Application No. PCT/EP2008/008547, mailed on Jun. 2, 2009; 12 pages.

* cited by examiner c)

d)

SYSTEM AND METHOD FOR EXAMINING AN ILLUMINATED OBJECT

CROSS-REFERENCES TO RELATED APPLICATIONS

This is application claims priority to and is a continuation-in-part of International Patent Application No. PCT/EP2008/008547, filed Oct. 9, 2008, which claims priority to German Patent Application No. DE 10 2007 048 362.9 filed Oct. 9, 2007, the disclosures of which are hereby incorporated by reference in their entirety.

BACKGROUND OF THE INVENTION

The present invention relates to a system and a method for examining an object. In particular, this invention relates to a system and a method for examining an object containing a flowing liquid. Further, this invention relates to a system and a method for examining a blood motion in a body part of a patient. In particular, this invention relates to a system and a method for displaying functional regions in a brain of a patient.

From the state of the art it is known to exploit the so-called "Doppler effect" to optically examine a motion of particles in a liquid. Thereby, measuring light is directed to a region of a body part of a patient to be examined. The measuring light penetrates some millimeters into the region to be examined and interacts with matter in the region within a penetration depth of the measuring light. Among other things, the measuring light is reflected from particles moving relative to each other, wherein the measuring light experiences a change of a wavelength compared to the wavelength of the measuring light being incident, wherein the change depends on the motion of the reflecting particles, in particular on the motion of blood cells. These changes of a wavelength of the reflected measuring light may be determined by detection using an appropriate detector. The basic principles for this so-called "laser Doppler method" are described in Stern, "In vivo evaluation of microcirculation by coherent light scattering", Nature, Vol. 254, pages 56-58, March 1975. Information about a motion of particles in a liquid are also referred to as perfusion data or perfusion in the following.

U.S. Pat. No. 4,109,647 describes how one may obtain information about the velocity of red blood cells at one point of a body part to be examined using this method.

U.S. Pat. No. 5,361,769 describes a scanning method for measuring blood perfusion of a body part to be examined. Thereby, a laser beam scans the body part to be examined, wherein the reflected signal is detected by a detector.

US 2005/0187477 A1 describes a laser-Doppler-perfusion imaging system to gain perfusion related data of a sample. The body part to be examined is illuminated across an area using laser light and the illuminated region is imaged to a detector extending in an area. From a plurality of such recorded images of the body part to be examined, information about a concentration of moving particles and about a velocity of particles moving relative to each other or relative to fixed structures in a sample volume which is associated to each pixel of the detector can be gained.

However, it became apparent that the previously described systems and methods often do not provide satisfying results.

For displaying and identifying functional regions in a brain of a patient so far a number of techniques have been used. In particular, it should be mentioned: functional magnet resonance tomography, electroencephalography, positron emission tomography and others. Due to the "blood oxygen level dependent (BOLD)-effect", it is possible in principle to detect a contrast in a body part to be examined due to the presence or non-presence of oxygenated and deoxygenated, respectively, hemoglobin using magnet resonance tomography. However, this method is very cost consuming and time consuming. Due to a long data recording time required by this method motions of the body part to be examined may occur during data recording. This in turn leads to difficulties in an evaluation of the data, in particular by the rotations and translations associated therewith, or also deformations of the data sets relative to each other which have to be determined to align the data relative to each other.

Thus, there is a need to provide a system and a method diminishing the above-mentioned disadvantages.

SUMMARY OF THE INVENTION

The present invention has been accomplished taking the above problems into consideration.

Therefore, it is an object of the present invention, to provide a system and a method for examining an object with which an examination of an object, in particular containing a flowing liquid, may be improved.

According to an embodiment of the present invention, a method for examining an object containing a flowing liquid is provided, wherein the method comprises: illuminating the object with measuring light and recording at least one sequence of first images of the illuminated object, wherein an exposure time for each recording of an image of the sequence of first images is smaller than 1 ms, in particular smaller than 0.1 ms, and further in particular smaller than 0.03 ms; evaluating the at least one sequence of first images (k=1, ..., N), by associating pixels (i,j) in the sequence of first images ($I_k(i,j)$) to which same locations (x,y) of the object are imaged with a first analysis image value, respectively, wherein the first analysis image value depends on temporal changes of image values ($I(t,i,j)$) of the pixels (i,j) in the at least one sequence of first images ($I_k(i,j)$) in a frequency range above 1 kHz, in particular above 10 kHz; and evaluating the at least one sequence of first images (k=1, ..., N) by further associating pixels (i,j) in the sequence of first images ($I_k(i,j)$) to which same locations (x,y) of the object are imaged with a second analysis image value, respectively, wherein the second analysis image value depends on temporal changes of image values ($I(t,i,j)$) of the pixels (i,j) in the at least one sequence of first images ($I_k(i,j)$) in a frequency range below 100 Hz, or a range of at most 25 Hz, or a range below 10 Hz.

An exposure time for each recording of an image of the sequence of first images is smaller than 1 ms, in particular smaller than 0.1 ms, and further in particular smaller than 0.03 ms. This is advantageous in order to prohibit that temporal oscillations of the received signals for each pixel of the image are averaged out over a time interval longer than 1 ms. Temporal changes of image values in a high frequency range above 1 kHz, in particular above 10 kHz, are used to obtain a first analysis image value for each pixel. Changes of image values in a low frequency range below 100 Hz, 25 Hz, or 10 Hz are used to obtain a second analysis image value for each pixel. The first analysis image value may comprise perfusion data of the illuminated object. Herein, in particular information about a concentration of particles moving relative to each other, about a velocity of particles moving relative to each other and about measures derived therefrom is comprised. Hereby, the second analysis image value represents temporal changes of image values in the low frequency range below 100 Hz. Thus, this second analysis image value is in particular sensitive to changes of detected intensities of light emanating from the object spanning a time interval of longer than 10 ms. Determining the second analysis image value may thereby comprise temporally filtering the image values to eliminate portions of high frequencies above 100 Hz from the temporal changes of the image values. The second analysis image value may also be obtained by selecting at least two images from the at least one sequence of first images and computationally combining the corresponding pixels. The second analysis is therefore useful to obtain information of actual changes of the state of the object, such as a change of the state of the subject's oxygenation. It is also envisaged to monitor an evolution of the state of the perfusion, i.e. an evolution of the first analysis image values over time, wherein the first analysis image values are themselves derived from (faster) temporal changes of the originally received signals for each pixel. Furthermore, averaging methods for averaging image values over certain time ranges (periods) may be applied. The end points of consecutive averaging periods may in some embodiments be selected so as to correspond to time differences larger than 10 ms, 40 ms or 100 ms, thereby reflecting temporal changes below 100 Hz, 25 Hz or 10 Hz, respectively.

According to an embodiment, temporal changes of image values are determined in two different time scales. Thus, processes occurring in these two different time scales may be examined in parallel, and independently of one another. While the first analysis image value may represent information about a motion of particles, in particular blood cells, in the illuminated object, the second analysis image value may represent other properties of the object, in particular (inherent) properties of a liquid flowing through the object, more particularly other properties than its flow speed. This may for example comprise a composition of the liquid, a concentration of certain particles or substances in the liquid, or a ratio of concentrations of two different particles (substances) within the liquid.

According to an embodiment of the present invention, the measuring light illuminating the object comprises wavelengths in a measuring light wavelength range from one of 605 nm to 630 nm, 560 nm to 580 nm, and 794 nm to 814 nm and the recording the first images comprises detecting measuring light, wherein a ratio of an intensity of the detected measuring light having wavelengths outside the measuring light wavelength range from a total intensity of the detected measuring light amounts to less than 10%.

In a wavelength range from 605 nm to 630 nm the deoxyhemoglobin absorbs at least three times stronger than oxyhemoglobin. Light of this wavelength range reflected from a body part filled with or flown through by blood may therefore indicate a ratio of deoxyhemoglobin and oxyhemoglobin in the blood. Thus, the second analysis image value may indicated a change of a degree of oxygenation of hemoglobin in the blood. Changes in the degree of oxygenation may indicate activities of muscle cells, nerve cells or organs of an examined body part of a patient. Thus, amongst the perfusion data derived from the first analysis image value, a further measured parameter is provided to examine blood flow and/or an oxygen transport in the blood. In particular, this may be advantageous for displaying and identifying functional regions in the brain of a patient. After stimulating or provoking the patient for example an increase of deoxyhemoglobin may be detected in certain regions of the brain, further an increase of the tissue perfusion leading to washing out the deoxyhemoglobin and thus leading to an increase of the oxyhemoglobin. Thus, a reaction of the organism in certain regions of the brain, for example in response to a stimulation, may be temporally examined, in particular with respect to a temporal chronology or a mutual causality of the different processes. Functional active regions may be for example a sensory region, a motor region, an acoustic region, a speech region, or a visual region, but also regions not yet known.

In a wavelength range from 560 nm to 580 nm, in particular at 570 nm and in a wavelength range between 794 nm to 814 nm, in particular at 804 nm, an isobestic point of the hemoglobin is located. At the isobestic point of the hemoglobin, oxyhemoglobin and deoxyhemoglobin absorb incident light of this wavelength to a same extent. Thus, detection in the aforementioned wavelength range allows to determine changes of a total hemoglobin content in the examined object. A total hemoglobin content may locally vary depending on an activity of cells, such as nerve cells, etc. Therefore, detection in the aforementioned measuring light wavelength range is also suited for examination of functional regions in the brain of a patient. In order not to receive disturbing signals, measuring light having wavelengths outside the measuring light wavelength range is largely prohibited to contribute to the detected measuring light.

According to an embodiment of the present invention, a method for examining an object containing a flowing liquid is provided, wherein the method comprises: illuminating the object with measuring light comprising wavelengths in a range from 790 nm to 820 nm; recording at least one sequence of first images of the illuminated object by a first detector, wherein an exposure time for each recording of an image of the sequence of first images is smaller than 1 ms, in particular smaller than 0.1 ms, and further in particular smaller than 0.03 ms; evaluating the at least one sequence of first images $(k=1, \ldots, N)$, by associating pixels $(i,j)$ in the sequence of first images $(I_k(i,j))$ to which same locations $(x,y)$ of the object are imaged with a first analysis image value, respectively, wherein the first analysis image value depends on temporal changes of image values $(I(t,i,j))$ of the pixels $(i,j)$ in the at least one sequence of first images $(I_k(i,j))$; and recording at least one second image of the illuminated object, wherein the second image is formed by detecting light having wavelengths in a range from 820 nm to 850 nm, in particular 830 nm to 840 nm, by a second detector and wherein a ratio of an intensity of light having wavelengths smaller than 820 nm detected by the second detector from a total intensity of light detected by the second detector amounts to less than 10%.

Indocyanin green absorbs light in a wavelength range from 790 nm to 820 nm, wherein a maximum of an absorption is at about 805 nm. Indocyanin green (ICG) is a fluorescence dye that may be injected into a blood stream of a patient. Indocyanin green fluoresces in a wavelength range from 800 nm to 900 nm, in particular between 820 nm and 850 nm, further in particular between 830 nm and 840 nm, wherein a fluorescence maximum is at about 835 nm. According to an embodiment of the present invention therefore the object is illuminated with measuring light which is suited to excite fluorescence emission of ICG. The excitation light is thereby used to obtain a first analysis image value according to another embodiment of the present invention which first analysis image value may represent perfusion data of the object containing a flowing liquid. By detecting within the fluorescence emission wavelength range by a second detector information about a concentration of ICG within the object containing a flowing liquid may be obtained. Again, it is thus possible using the inventive method to simultaneously determine two parameters carrying independent information about a flowing liquid.

According to an embodiment, the recording the at least one sequence of first images by the first detector comprises detecting measuring light in a wavelength range from 790 nm to 820 nm.

According to an embodiment of the present invention, a method for examining an object containing a flowing liquid is provided, the method comprising: illuminating the object with measuring light and recording at least one sequence of first images of the illuminated object, wherein an exposure time for each recording of an image of the sequence of first images is smaller than 1 ms, in particular smaller than 0.1 ms, and further in particular smaller than 0.03 ms; evaluating the at least one sequence of first images (k=1, ..., N) by associating pixels (i,j) in the sequence of first images ($I_k(i,j)$) to which same locations (x,y) of the object are imaged with a first analysis image value, respectively, wherein the first analysis image value depends on temporal changes of image values (I(t,i,j)) of the pixels (i,j) in the at least one sequence of first images ($I_k(i,j)$), wherein the recording the at least one sequence of first images of the illuminated object comprises detecting measuring light in a first predetermined wavelength range from one of 560 nm to 580 nm, 605 nm to 630 nm, and 794 nm to 814 nm, wherein a ratio of an intensity of detected measuring light having wavelengths outside the first predetermined wavelength range from a total intensity of detected measuring light is smaller than 10%.

Similar as in other embodiments of the present invention perfusion data about the object containing a flowing liquid may be gained from the first analysis image value. It is advantageous to use measuring light in a first predetermined wavelength range from 560 nm to 580 nm or from 605 nm to 630 nm or from 794 nm to 814 nm. Thereby, beside the perfusion data, information about a degree of oxygenation of hemoglobin in the blood or about a total concentration of hemoglobin in the blood may be gained.

According to an embodiment of the invention, the method further comprises: recording at least one second image of the illuminated object by detecting measuring light in a second predetermined wavelength range from 560 nm to 580 nm or from 605 nm to 630 nm or from 794 nm to 814 nm, wherein a ratio of an intensity of detected measuring light having wavelengths outside the second predetermined wavelength range from a total intensity of detected measuring light is smaller than 10%, wherein the first predetermined wavelength range is different from the second predetermined wavelength range.

Thereby, measuring light is detected in a second predetermined wavelength range which second predetermined wavelength range is different from the first predetermined wavelength range. Thus, it is possible to simultaneously determine a degree of oxygenation of hemoglobin as well as a total concentration of hemoglobin in the object.

According to an embodiment of the present invention, the method further comprises evaluating the at least one sequence of first images (k=1, ..., N) by further associating pixels (i,j) in the sequence of first images ($I_k(i,j)$) to which same locations (x,y) of the object are imaged with a second analysis image value, respectively, wherein the second analysis image value depends on temporal changes of image values (I(t,i,j)) of the pixels (i,j) in the at least one sequence of first images ($I_k(i,j)$) in a frequency range below 100 Hz, up to 25 Hz, or below 10 Hz.

Using this method, it is thus possible to detect temporal changes of an ICG concentration, temporal changes of a degree of oxygenation and temporal changes of a total hemoglobin content in the object, which occur on a relatively slow time scale. It is also possible to evaluate first analysis image values for each of subsequent time periods of at least 10 ms in length, and to then evaluate a temporal evolution of such consecutive first analysis image values, as the second analysis image values, both for each pixel.

According to an embodiment of the present invention, the first analysis image value associated to pixels (i,j) in the sequence of first images, respectively, is dependent on temporal changes of image values of the pixels in the at least one sequence of first images in a frequency range above 1 kHz, in particular above 10 kHz.

According to an embodiment of the present invention, the recording the at least one sequence of first images comprises recording of temporally subsequent images having a temporal interval of smaller than 1 ms, in particular smaller than 0.1 ms, and further in particular smaller than 0.05 ms. Thus, it is possible to sample and detect a light signal emanating from the object that fast such that the detected image values comprise temporal changes of the light signals in a frequency range up to at least 10 kHz.

According to an embodiment of the present invention, the recording the first images comprises detecting measuring light, wherein the ratio of an intensity of the detected measuring light having wavelengths larger than 850 nm and smaller than 500 nm from a total intensity of the detected measuring light amounts to less than 10%.

According to an embodiment of the present invention, the measuring light exhibits a coherence length corresponding to at least twice a penetration depth of the measuring light into the object. A penetration depth of the measuring light into the object refers to a path within the object, wherein upon traversal of the measuring light through this path of the object an intensity of the measuring light drops to a fraction of 1/e ($1/2.71828$) of an intensity of light being incident onto the object. A coherence length of the measuring light is an average length of a continuous wave train. Portions of such a wave train are in a fixed phase relation relative to each other and thus may form a defined interference pattern upon superposition. Thus, according to this embodiment, measuring light on one hand being reflected at the surface of the object and on the other hand being reflected at a layer situated deeper by the penetration depth can interfere with each other. Thus, reflected light capable of interference evolves from a depth within the object corresponding to the penetration depth of the measuring light.

According to an embodiment of the present invention, the method further comprises illuminating the object with white light and imaging and detecting the object illuminated with white light to determine a white light image of the object. By this provision, the parameters determined from the first analysis image values and the second analysis image values and the second image can be put in relation to structures of the object, in particular organs, identifiable in the visible light. Thereby, it is for example possible to correlate regions of high or low perfusion, regions of high or low ICG concentration, regions of high or low oxygenation or regions of high or low hemoglobin concentration with blood vessels or other relevant structures of an examined body part. These images may also be supplied to a microscope, in particular a surgical microscope, by known techniques. Besides the perfusion data, functional region determined therefrom, ICG concentration data, data of a degree of oxygenation, also preoperatively acquired data, such as nuclear spin data, functional nuclear spin data or x-ray data may be supplied for concurrent display.

According to an embodiment of the present invention, the first analysis image value associated to a pixel represents a value comprising one of a perfusion, a concentration, an average velocity, and a measure for a velocity distribution, in particular a standard deviation of the velocity distribution, of particles moving relative to each other, in particular blood cells, and a combination of the former.

The detected temporal changes of image values may be caused by reflection of measuring light from a plurality of particles moving relative to each other and subsequent superposition. A motion of a particle with a particular velocity involves that light reflected from this particle exhibits a wavelength different from the wavelength of the incident light. This change in the wavelength involves a change in the frequency of the light reflected from the moving particle. In particular, this frequency shift $\Delta\omega$(=$2\pi$ times the difference between the frequencies of the incident and reflected light) is $$\Delta\omega = \bar{k} \cdot \bar{v},$$

wherein $\bar{k}$ is the wave vector ($2\pi/\lambda$) of the light having wavelength $\lambda$ and $\bar{k}$ is the velocity of the particle with respect to a light source emitting the measuring light.

The fluctuations or temporal changes of the detected image values represent frequency shifts of reflected measuring light being reflected from moving particles. From the image values a spectrum of frequency shifts may be obtained. This may comprise applying Fourier methods. Determining a concentration of particles moving relative to each other may comprise integrating the spectrum of the frequency shifts. Determining a perfusion may comprise computing a first moment of the spectrum of the frequency shifts. Determining an average velocity may comprise forming a ratio of a perfusion and a concentration.

According to an embodiment of the present invention, the method further comprises at least one of displaying, in particular in superposition, and storing at least one of the first images, the first analysis image values, the second analysis image values, and the white light image for a plurality of pixels.

According to an embodiment of the present invention, the method further comprises repeating the recording the sequence of first images as temporal sequence and respectively evaluating the repeatedly recorded sequence of first images.

According to an embodiment of the present invention, the object is a part of a brain of a patient, in particular an aneurysm in the head of the patient. Using the inventive method, functional region in the brain of a patient may be effectively displayed or identified. Herein, it is in particular advantageous to be provided with several independent parameters (first analysis image value, second analysis image value, second image), to perform a more accurate analysis. For examining an aneurysm in the head of a patient in particular a method according to an embodiment of the present invention may be applied.

According to an embodiment, the method further comprises stimulating the patient. The stimulating may thereby comprise requesting to perform a particular action, requesting to speak a word, requesting to move a hand or a finger or the like. The stimulating may be an acoustic stimulating, visual stimulating or may be causing pain. The stimulating may thereby be repeatedly performed, in equal or not equal intervals, wherein regular or irregular sections of a pause may be inserted.

According to an embodiment of the present invention, the method further comprises: displaying a region of the object in dependence of a result of comparing one of the first analysis value, the second analysis value, and the image value of the at least one second image with preset threshold values for pixels to which the region of the object is imaged.

For example, functional regions in a brain of a patient may be identified by detecting that one of the first analysis value, the second analysis value and the image value of the at least one second image exceeds or falls below preset threshold values. This may indicate that a perfusion (obtained from a first analysis value), a degree of oxygenation, a hemoglobin concentration or a ICG concentration or their temporal changes or evolution (obtained from a second analysis value) are above or below an expected (e.g. critical) value.

According to an embodiment of the present invention, the method further comprises injecting indocyanin green into a blood stream of a patient.

According to an embodiment of the present invention, a system for examining an object is provided, wherein the system comprises: a light source for illuminating the object with measuring light; a first detector for recording at least one sequence of first images of the illuminated object, wherein an exposure time for a recording of an image of the sequence of first images is adjustable to be smaller than 1 ms, in particular smaller than 0.1 ms, and further in particular smaller than 0.03 ms; an evaluation system for evaluating the at least one sequence of first images (k=1, . . . , N), wherein the evaluation system is adapted to associate pixels (i,j) in the sequence of first images ($I_k(i,j)$) to which same locations (x,y) of the object are imaged with a first analysis image value, respectively, wherein the first analysis image value depends on temporal changes of the image values (I(t,i,j)) of the pixels (i,j) in the at least one sequence of first images ($I_k(i,j)$) in a frequency region above 1 kHz, in particular above 10 kHz, wherein the evaluation system is further adapted to associate pixels (i,j) in the sequence of first images ($I_k(i,j)$) to which same locations (x,y) of the object are imaged with a second analysis image value, respectively, wherein the second analysis image value depends on temporal changes of the image values (I(t,i,j)) of the pixels (i,j) in the at least one sequence of first images ($I_k(i,j)$) in a frequency range below 100 Hz, up to 25 Hz or below 10 Hz.

According to an embodiment of the present invention, the system further comprises a first filter for spectrally filtering light for recording images of the illuminated object by the first detector, wherein the first filter is configured such that a ratio of an intensity of light outside a measuring light wavelength range from 605 nm to 630 nm, 560 nm to 580 nm, or 794 nm to 814 nm emanating from the filter from a total intensity of light outside this wavelength range being incident onto the first filter amounts to less than 10%.

Such a configured first filter allows to detect measuring light which is, besides the determination of a perfusion, suitable for determination of a degree of oxygenation of hemoglobin or for determination of a total concentration of hemoglobin. Disturbing light wavelengths are thus efficiently suppressed.

According to an embodiment of the present invention, a system for examining an object is provided, the system comprising: a light source for illuminating the object with measuring light comprising wavelengths in a range from 790 nm to 820 nm; a first detector for recording at least one sequence of first images of the illuminated object, wherein an exposure time for a recording of an image of the sequence of first images is adjustable to be smaller than 1 ms, in particular smaller than 0.1 ms, and further in particular smaller than 0.03 ms; an evaluation system for evaluating the at least one sequence of first images (k=1, . . . , N), wherein the evaluation system is adapted to associate pixels (i,j) in the sequence of first images ($I_k(i,j)$) to which same locations (x,y) of the object are imaged with a first analysis image value, wherein the first analysis image value depends on temporal changes of image values (I(t,i,j)) of the pixels (i,j) in the at least one sequence of first images ($I_k(i,j)$), wherein the system further comprises: a second detector for detecting light having wavelengths in a range from 820 nm to 850 nm, in particular 830 nm to 840 nm, wherein the second detector is arranged for recording at least one second image of the illuminated object and is configured such that light in a first wavelength range between 820 nm and 850 nm having an initial intensity emanating from the illuminated object along a beam path in a direction towards the second detector is detected by the second detector as a first intensity and such that light in a second wavelength range between 790 nm and 820 nm having the initial intensity emanating from the illuminated object along the beam path in the direction towards the second detector is detected by the second detector as a second intensity, wherein the first intensity is ten times higher than the second intensity.

The system is suited to excite a fluorescence of indocyanin green (ICG). The second detector is configured to detect fluorescence light emitted by ICG, wherein excitation light in the wavelength range between 790 nm and 820 nm is detected with ten times lower sensitivity than fluorescence light in a wavelength range from 820 nm to 850 nm.

According to an embodiment of the present invention, a first filter is arranged in a beam path of the measuring light in a direction of travelling of the measuring light in front of the first detector, wherein a ratio of an intensity of light in a wavelength range between 820 nm and 850 nm emanating from the first filter from a total intensity of light outside the wavelength range being incident onto the first filter amounts to less than 10%.

According to an embodiment of the present invention, the second detector comprises a second filter arranged in a beam path of the measuring light in a direction of travelling of the measuring light in front of the second detector, wherein a ratio of an intensity of light in a wavelength range between 820 nm and 790 nm emanating from the second filter from a total intensity of light in the wavelength range being incident onto the second filter amounts to less than 10%.

According to an embodiment of the present invention, a system for examining an object is provided, the system comprising: a light source for illuminating the object with measuring light; a first detector for recording at least one sequence of first images of the illuminated object, wherein an exposure time for a recording of an image of the sequence of first images is adjustable to be smaller than 1 ms, in particular smaller than 0.01 ms, and further in particular 0.03 ms; an evaluation system for evaluating the at least one sequence of first images (k=1, ..., N), wherein the evaluation system is adapted to associate pixels (i,j) in the sequence of first images ($I_k(i,j)$) to which same locations (x,y) of the object are imaged with a first analysis image value, respectively, wherein the first analysis image value depends on temporal changes of image values ($I(t,i,j)$) of the pixels (i,j) in the at least one sequence of first images ($I_k(i,j)$), wherein the first detector is adapted to detect measuring light in a first predetermined wavelength range from 560 nm to 580 nm or from 605 nm to 630 nm or from 794 nm to 814 nm and wherein the first detector is configured such that light in the first predetermined wavelength range having an initial intensity emanating from the illuminated object along a beam path in a direction towards the first detector is detected by the first detector as a first intensity and such that light outside the first predetermined wavelength range having the initial intensity emanating from the illuminated object along the beam path in the direction towards the first detector is detected by the first detector as a second intensity, wherein the first intensity is ten times, in particular one hundred times higher than the second intensity.

The system is suited to determine perfusion data as well as data about a degree of oxygenation or a total content of hemoglobin concurrently for the same object region.

According to an embodiment of the present invention, the system further comprises a second detector for recording at least one second image of the illuminated object, wherein the second detector is adapted to detect measuring light in a second predetermined wavelength range from 560 nm to 580 nm or from 605 nm to 630 nm or from 794 nm to 814 nm and wherein the second detector is configured such that light in the second predetermined wavelength range having a further initial intensity emanating from the illuminated object along a beam path in a direction towards the second detector is detected as a further first intensity and such that light outside the second predetermined wavelength range having the further initial intensity emanating from the illuminated object along the beam path in the direction towards the second detector is detected by the second detector as a further second intensity, wherein the further first intensity is ten times, in particular one hundred times higher than the further second intensity and wherein the first predetermined wavelength range is different from the second predetermined wavelength range.

By this provision it is possible to determine perfusion data as well as also data about a degree of oxygenation and data about a total content of hemoglobin.

According to an embodiment of the present invention, the evaluation system is further adapted to associate pixels (i,j) in the sequence of first images ($I_k(i,j)$) to which same locations (x,y) of the object are imaged with a second analysis image value, respectively, wherein the second analysis image value depends on temporal changes of image values ($I(t,i,j)$) of the pixels (i,j) in the at least one sequence of first images ($I_k(i,j)$) in a frequency range below 100 Hz, up to 25 Hz, or below 10 Hz.

Thereby, temporal changes of a concentration of ICG after injection, of a degree of oxygenation and a total content of hemoglobin may be determined, these quantities normally varying appreciably (e.g., by 10% of a maximum) relatively slowly.

According to an embodiment of the present invention, the first analysis image value respectively associated with pixels in the sequence of first images is dependent of temporal changes of image values of the pixels of the at least one sequence of first images in a frequency range above 1 kHz, in particular above 10 kHz.

According to an embodiment of the present invention, the first detector comprises a first filter arranged in a beam path of measuring light detected by the first detector, wherein a ratio of an intensity of light outside the first predetermined wavelength range emanating from the first filter from a intensity of light outside the first predetermined wavelength range being incident onto the filter amounts to less than 10%.

According to an embodiment of the present invention, the evaluation system comprises a low path filter to determine temporal changes of image values of the pixels in the at least one sequence of first images in a frequency range below 100 Hz, up to 25 Hz, or below 10 Hz.

According to an embodiment of the present invention, the evaluation system is adapted to record images having a temporal interval of smaller than 1 ms, in particular smaller than 0.1 ms, and further in particular smaller than 0.05 ms.

For example, providing a detector allowing to record images having a temporal interval of 0.05 ms, allows a detection of measuring light signals in a frequency range up to 10 kHz. Thus, the detected image values represent a light signal sampled with a sampling frequency of 20 kHz. A maximal velocity of a moving particle that may be determined using such a detector is 4 mm/s when utilizing measuring light having a wavelength of 800 nm. This velocity approximately corresponds to blood flow velocities in capillaries and microcapillaries of a patient.

According to an embodiment of the present invention, the light source is adapted to generate light having wavelengths in the region from 500 nm to 850 nm.

According to an embodiment of the present invention, the light source is adapted to generate light having a coherence length, comprising a temporal coherence length, of greater than 2 mm.

According to an embodiment of the present invention, the system further comprises an illumination apparatus for illuminating the object with white light and an imaging apparatus for imaging the object illuminated with white light to a white light image of the object and further a display apparatus for displaying images, in particular in superposition.

According to an embodiment of the present invention, the system further comprises a storage system for storing at least one of first images of the illuminated object, first analysis image values, second analysis image values, the second image and the white light image.

According to an embodiment of the present invention, the system further comprises a display apparatus for displaying at least one of the recorded first images, the first analysis image values, the second analysis image values, the second image, and the white light image.

BRIEF DESCRIPTION OF THE DRAWINGS

The foregoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1:
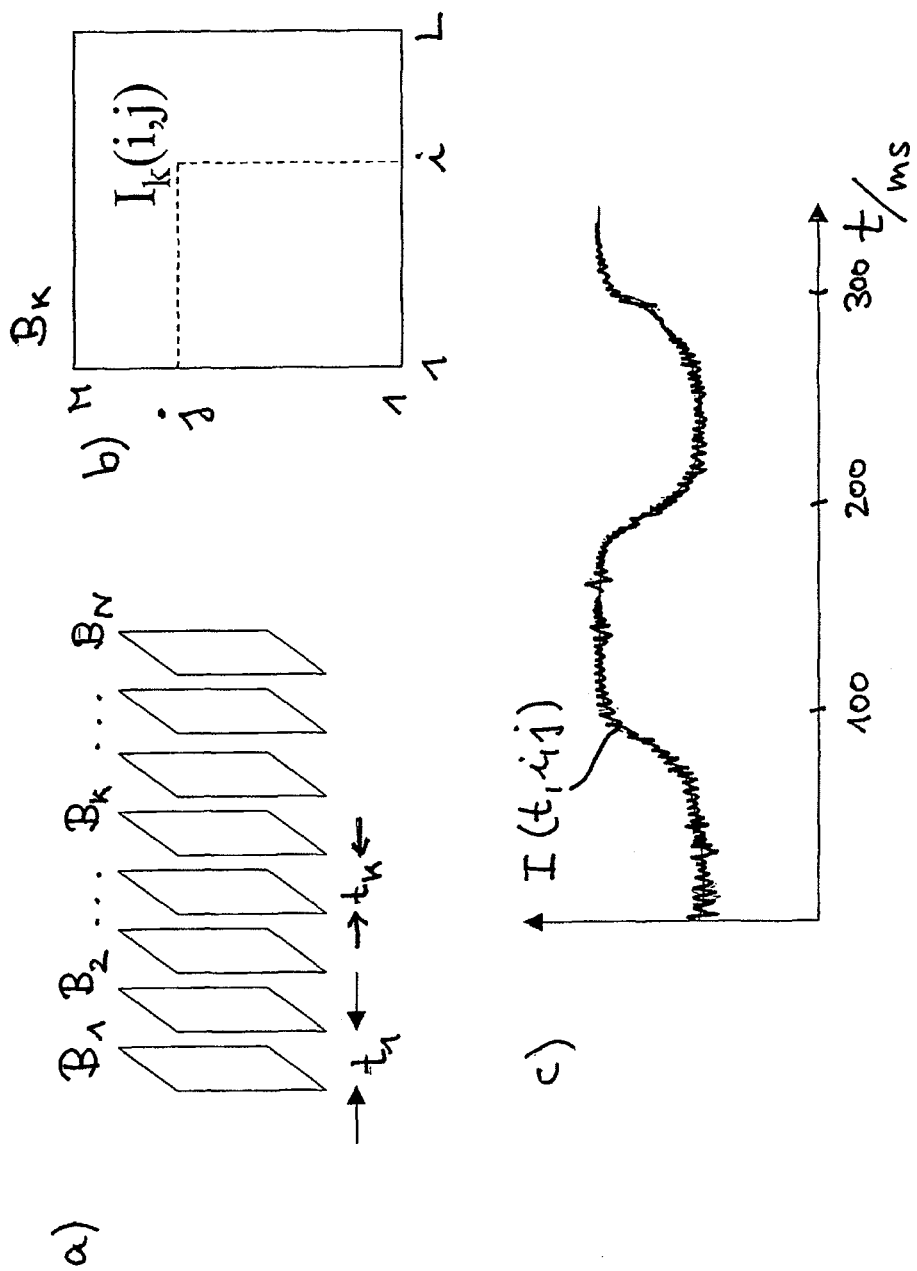
FIG. 1 illustrates an embodiment of a method for examining an object according to the invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 shows a method for examining an object according to an embodiment of the present invention. A sequence of images $B_1, \ldots, B_k, \ldots, B_N$ is recorded from an object illuminated with measuring light. A temporal interval t1 between the recording of the first image $B_1$ and the recording of the second image $B_2$ amounts to 0.05 ms. The sequence of images $B_1, \ldots, B_k, \ldots, B_N$ is illustrated in FIG. 1a. The image $B_k$ is illustrated in FIG. 1b. Every image $B_k(k=1, \ldots, N)$ is described by image values $I_k(i,j)$), wherein (i,j) denote indices of the pixels of the detector arranged in an area. The image $B_k$ has an image value $I_k(i,j)$) at the location defined by the indices i and j. In the illustrated example the first index of the pixels of the image runs from 1 to L and the second index of the pixels of the image runs from 1 to M. Using the temporal distances between the recordings of two subsequent images for every pixel (i,j) of the sequence of images a temporal course of image values I(t,i,j) may be obtained. An example of such a temporal course of image values I(t,i,j) is illustrated in FIG. 1c. In this Figure, the image value I(t,i,j) of a pixel (i,j) is plotted versus the time t. It is apparent that the temporal course I(t,i,j) comprises changes or fluctuations which are temporarily spaced apart less than 1 ms (high frequency portion of the temporal changes of the image values) which are superimposed by temporal changes which are temporarily spaced apart in the order of 10 ms or greater (low frequency portion of the temporal changes of image values) or even 40 ms or greater or 100 ms or greater. Temporal changes of image values being temporally spaced apart shorter than 0.5 ms are comprised in the image values but are not illustrated here. Temporal changes of image values being spaced apart longer than 1 s or 10 s are comprised in the temporal changes of the image values but are not illustrated due to the chosen section of a temporal development of image values.

Figure 2:
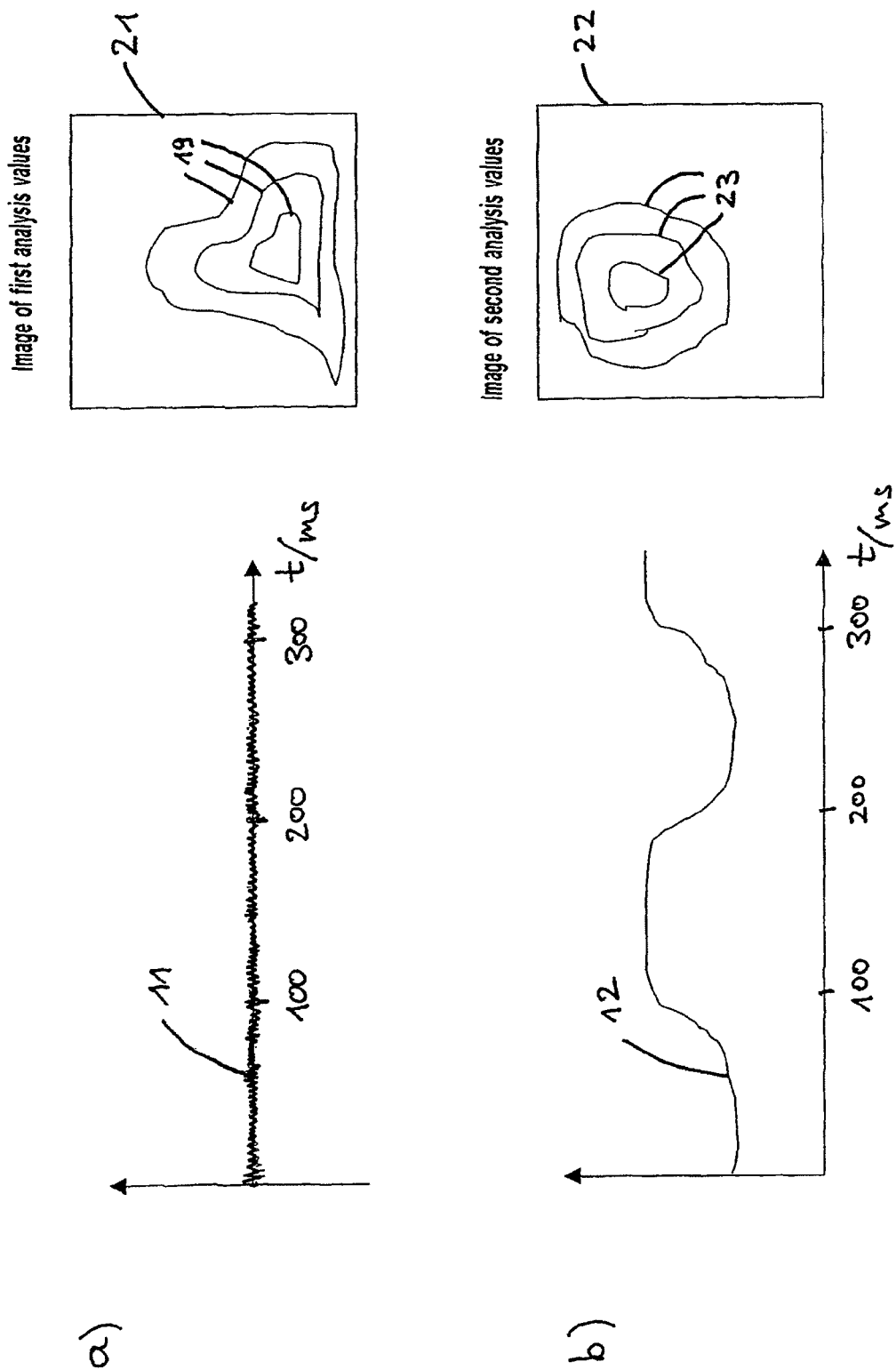
FIG. 2 illustrates an evaluation method of a method for examining an object according to an embodiment of the present invention.

FIG. 2 schematically illustrates an evaluation method according to an embodiment of the present invention. The left hand side of FIG. 2a illustrates as a graph 11 temporal changes of images values in a frequency range above 1 kHz, in the following also denoted as high frequency range of temporal changes of the image values, or simply high frequency range. In particular this portion of temporal changes of image values carries information about a motion of particles within the illuminated object from which measuring light was reflected. A further evaluation of this high frequency portion of temporal changes of image values comprises establishing a Fourier spectrum or power spectrum of temporal changes of image values. The Fourier spectrum or the power spectrum may further be analyzed with respect to its moments. Thereby, moments of this spectrum are for example an average value or an area. From the moments of the Fourier spectrum or power spectrum a concentration of particles moving relative to each other, a velocity of particles moving relative to each other and a perfusion of these particles may be obtained which parameter are denoted as first analysis values. When the afore-explained analysis of temporal changes of image values in the high frequency range is performed for every pixel of the sequence of images, $B_1, \ldots, B_k, \ldots, B_N$ an image 21 of first analysis values is obtained as illustrated in the right hand side of FIG. 2a. The values of first analysis values within the image 21 of first analysis values are illustrated as contour lines 19 in the illustrated example. FIG. 2b shows a further evaluation step of the inventive method. On the left hand side in FIG. 2b the temporal course of image values I(t,i,j) of the temporal course of image values illustrated in FIG. 1c is illustrated in a frequency range below 100 Hz as curve 12. Thus, the curve 12 does not comprise anymore the very fast temporal changes of image values occurring in time intervals below 1 ms, in particular 0.1 ms. Depending on the application and on the object to be examined the temporal changes of image values may be analyzed in different low frequency ranges, such as below 1 Hz, below 10 Hz, below 25 Hz or below 100 Hz. Thereby, the curve 12 may be determined in different manners. For example it is possible, to apply a low pass filter to the image value I(t,i,j) to obtain the curve 12. Alternatively, at least two images may be selected from the sequence of images $B_1, \ldots, B_k, \ldots, B_N$ to obtain the curve 12. This may for example also comprise interpolation methods to determine values of image values at intermediate locations not measured. From the values or temporal changes of the curve 12 an image 22 of second image values is obtained again showing contour lines 23. It is apparent that a shape of the contour lines 19 of the image 21 have a form different from a form of the contour lines 23 of the image 22 in FIG. 2.

Figure 3:
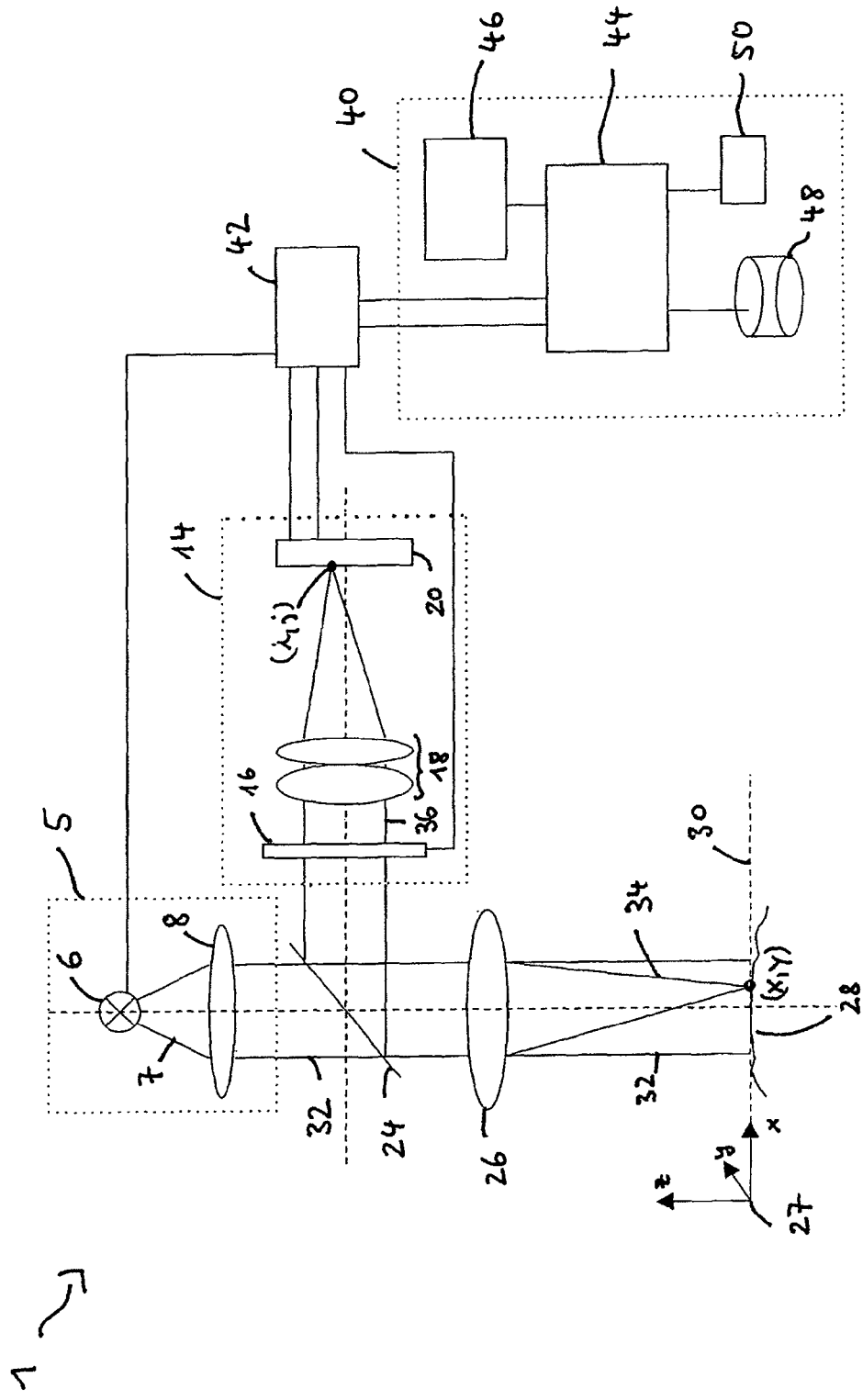
FIG. 3 illustrates a system for examining an object according to an embodiment of the present invention.

FIG. 3 illustrates a system 1 for examining an object according to an embodiment of the present invention. The system 1 comprises an illumination apparatus 5, a beam splitter 24, an objective 26, a position acquisition apparatus 27, a first camera 14, a controller 42, and an evaluation system 40. The illumination apparatus 5 comprises a laser 6 for generating light having a coherence length of at least 2 mm. Preferably, the laser 6 is tunable to be able to generate laser light having different wavelengths. The light 7 generated by the laser 6 is collimated by the collimator 8 to form measuring light 32. Measuring light 32 traverses the semi-transparent mirror 24 and the objective 26 to illuminate the object 28 in the object plane 30 with measuring light 32. A position (x,y) of the object 28 is registered by the position acquisition apparatus 27 thereby allowing a conversion of coordinates in an object coordinate system into coordinates of a coordinate system of the system 1. Thereby, it is in particular possible to convert coordinates in images of the object generated from the first camera 14 into coordinate of a coordinate system of the object. The light 34 emanating from a point (x,y) of the object 28 traverses the objective 26 and is reflected at the semi-transparent mirror 24 to enter the first camera 14. The first camera 14 comprises a first filter 16 to filter out undesired wavelengths from the light 34 emanating from the object or to filter out stray light from the surrounding. The filtered light 36 traverses the camera optics 18 imaging the filtered light 36 to a pixel (i,j) of the first detector 20. Different locations of the object 28 thus are imaged to different pixels of the first detector. The first detector 20 is capable to record images having an exposure time of 0.05 ms. A temporal interval between recordings of two images amounts to 0.1 ms. The first detector 20 and also the first filter 16 are connected with the camera controller 42. The camera controller 42 is capable to send signals to the first filter 16 to change a filter characteristics of the first filter 16. This may for example be realized in that a wheel having different filters arranged in a circumferential direction is rotated to bring a desired filter into a beam path of the first camera 14. Correspondingly, the controller 42 may control the tunable laser to choose a desired wavelength of the measuring light 32. Depending on the object 28 to be examined measuring light having different wavelengths may be advantageous for examining the object. Wavelengths in a measuring light wavelength range from 605 nm to 630 nm, 560 nm to 580 nm or 794 nm to 814 nm may be utilized to measure a degree of oxygenation of hemoglobin or to measure a concentration of hemoglobin within the sample. Images recorded by the first detector are acquired by the controller 42 and transferred to the evaluation system 40. The evaluation system 40 comprises a processing system 44, a display device 46, a storage system 48 and an input system 50. The processing system 44 comprises a computer capable of running image processing software. The image processing software enables to read in a sequence of images generated by the first detector 20. The software is adapted to evaluate the sequence of images per pixel to analyze temporal changes of image values I(t,i,j). The image processing software is controlled via the input system 50 comprising a console and a cursor. On the display device 46 comprising a screen the course of the analysis of the sequence of images may be monitored. The evaluating the sequence of images per pixel comprises computing a spectrum of the temporal changes of image values and computing moments of this spectrum. Further, the temporal changes of image values are filtered with respect to their frequency range. Result images of the analysis may be displayed on the display device 46, in particular in superposition. Thereby, it is for example possible, to display perfusion data of the examined object together with degrees of oxygenation or total concentrations of hemoglobin, wherein those parameters are concurrently determined by the inventive system 1. If the temporal behavior of the second analysis values is more closely examined, a more accurate analysis of different aspects of the object is concurrently possible, such as a correlation of the perfusion with a breathing rate. These images and other data may also be supplied for display into a surgical microscope.

Figure 4:
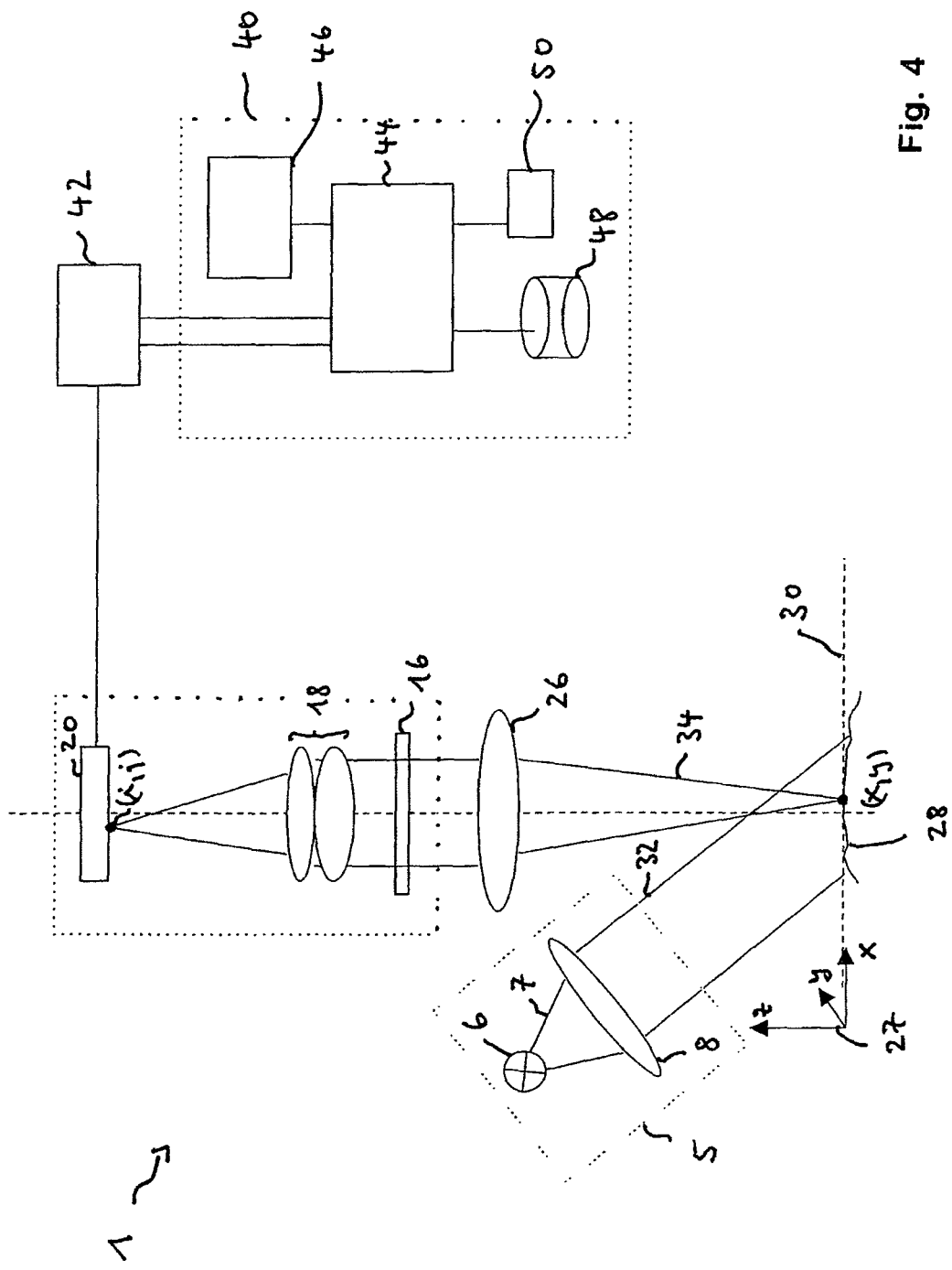
FIG. 4 illustrates a further system for examining an object according to an embodiment of the present invention.

FIG. 4 shows a system 1 for examining an object according to an embodiment of the present invention. In contrast to the embodiment illustrated in FIG. 3, the light 7 emitted by the laser 6 being collimated by the collimator 8 and leaving same as measuring light 32 does not travel along a common beam path together with the light 34 emanating from the object 28. Other elements of the system 1 illustrated in FIG. 4 are analogous to those of the system 1 illustrated in FIG. 3 and thus a repeated description is avoided.

Figure 5:
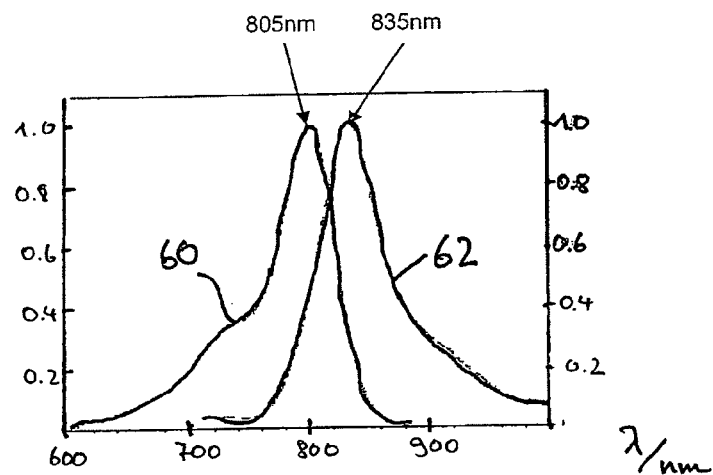
FIG. 5 illustrates an absorption spectrum and a fluorescence emission spectrum of indocyanin green (ICG)

FIG. 5 illustrates an excitation spectrum and a fluorescence emission spectrum of indocyanin green (ICG). Curve 60 shows an excitation spectrum of ICG, wherein a normalized absorption is plotted versus a wavelength. ICG absorbs light in a wavelength range from about 700 nm to 850 nm. Thereby, a maximum of absorption occurs at around 805 nm. By illuminating ICG with light between 790 nm and 820 nm a fluorescence emission of ICG is excited. Curve 62 shows a fluorescence emission spectrum of ICG, wherein a normalized fluorescence is plotted against a wavelength. It is apparent that ICG is fluorescent in a wavelength range from about 800 nm to 900 nm. A maximum of fluorescence emission is observed at around 835 nm. To detect a content of ICG within a sample using fluorescence of ICG it is thus necessary to illuminate the sample with light in a wavelength range from about 790 nm to 820 nm and to determine a fluorescence intensity by detection of light having wavelengths between 820 nm and around 850 nm emanating from the sample.

Figure 6:
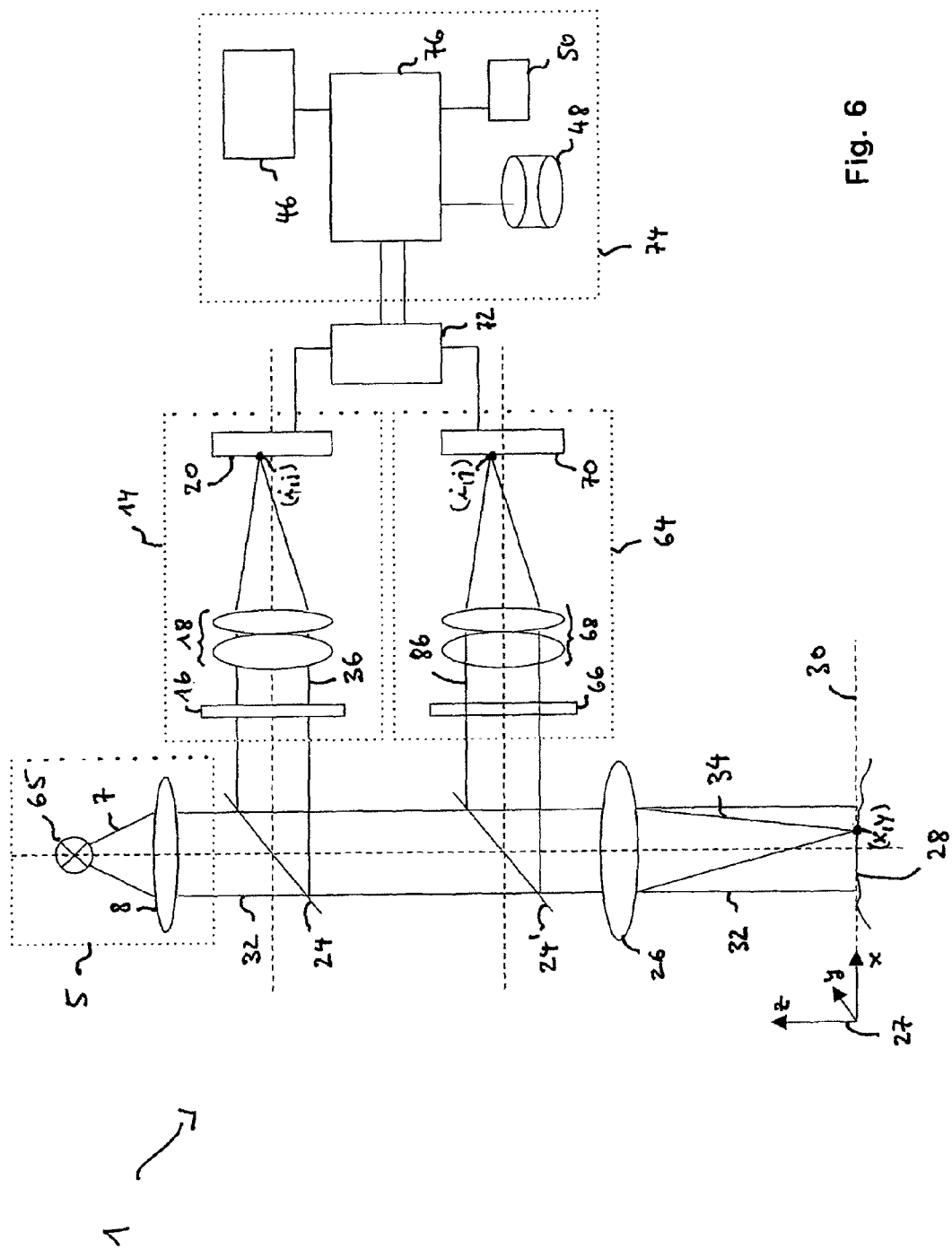
FIG. 6 illustrates a system for examining an object according to an embodiment of the present invention.

FIG. 6 illustrates a system 1 for examining an object according to an embodiment of the present invention. The system 1 comprises an illumination apparatus 5, a semi-transparent mirror 24, a semi-transparent mirror 24', an objective 26, a first camera 14, a second camera 64 and an evaluation system 74. The illumination apparatus 5 comprises a laser 65 capable to generate light in a wavelength range from 790 nm to 820 nm. The light 7 emitted by the laser 65 is collimated by the collimator 8 to form measuring light 32. Measuring light 32 traverses the semi-transparent mirror 24 and the semi-transparent mirror 24' to traverse the objective 26 and illuminate the object 28. Light 34 emanating from the illuminated object traverses the objective 26 and impinges onto the semi-transparent mirror 24' at which a portion of the impinging light is reflected to enter the second camera 64. Another portion of the light impinging onto the semi-transparent mirror traverses the same and is reflected at the semi-transparent mirror 24 to enter the first camera 14. The first camera 14 comprises a first filter 16 having a transmission characteristics to allow traversing light having wavelengths suited for excitation of fluorescence of ICG, i.e. in a wavelength range between 790 nm and 820 nm, as filtered light 36. Filtered light 36 traverses the camera optics 18 to be imaged onto a pixel (i,j) of the first detector. The first detector 20 is capable to record images having an exposure time of 0.05 ms. A temporal interval between the recordings of two images amounts to 0.1 ms. The light entering the second camera 64 having emanated from the location (x,y) of the object 28 as light 34 traverses a second filter 66 which is designed to attenuate light used for excitation of fluorescence emission of ICG, i.e. light having wavelengths between 790 nm and 820 nm, upon traversal through the filter 66 strongly in its intensity. In particular, the filter 66 is designed such that only 10% of an intensity of light in a wavelength range between 790 nm and 820 nm is allowed to traverse. On the other hand, the filter 66 is transparent for fluorescence light of ICG, i.e. transparent in a wavelength range between about 820 nm and 850 nm. The filtered light 86 emanating from the filter 66 traverses the camera optics 68 to be imaged onto a pixel (i,j) of the second detector 70. While, as described above, the first detector 20 is capable to subsequently record images having a very short temporal interval (0.1 ms), the second detector 70 records images having much larger temporal intervals (larger than 10 ms). Thus, a CCD-detector may be employed as a second detector 70. The first detector 20 however may be a CMOS-detector. The controller 72 controls the recording of images of the first detector 20 as well as images of the second detector 70 and acquires the thus obtained first and second images. The first and second images are provided to the evaluation system 74, in particular to the processing system 76. The processing system 76 comprises as the processing system 44 of the embodiment illustrated in FIG. 3 an image processing software. The image processing software is however also configured to process second images generated by the second detector 70. The processing the images acquired by the first detector 20 is simplified in comparison to the processing of the first images of the embodiment illustrated in FIG. 3. In the embodiment shown in FIG. 6 not necessarily second analysis image values must be determined from a sequence of recorded first images, wherein the second analysis image values depend on temporal changes of image values in the sequence of first images in a frequency range below 100 Hz. However, as in the embodiment illustrated in FIG. 3, first analysis values are determined from the temporal changes of image values of the sequence of recorded first images, wherein the first analysis values represent perfusion data. Thus, also in this embodiment, information about a motion of particles within the illuminated object are determined. Due to the choice of the measuring light being suited for excitation of a fluorescence of ICG, and the choice of the filter characteristics of the second filter 66, the second detector 70 substantially detects fluorescence light of ICG emanating from the object 28.

The embodiments illustrated in the FIGS. 3, 4 and 6 may further comprise a system for imaging the object as white light image. Such a white light imaging system may comprise an illumination source such as a halogen lamp, an objective, and a further detector such as a CCD camera. The white light imaging system may also be adapted as a microscope, in particular as a surgical microscope. Images generated by the white light imaging system may be provided to the evaluation system 40 and 74, respectively, and may be displayed together with the first and second images, the first and second analysis image values by the display device 46 or/and may be supplied for display in the surgical microscope.

Figure 7A:
FIG. 7a illustrates a white light image.
Figure 7B:
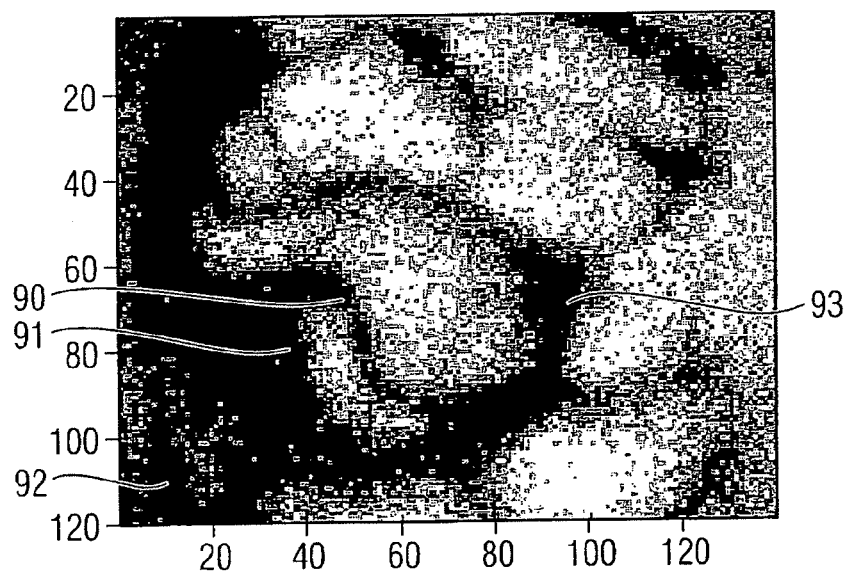
FIG. 7b illustrates an image of first analysis values (perfusion data) of an object, wherein the images were determined according to a method for examining an object according to an embodiment of the present invention.

FIG. 7 shows images determined using systems according to embodiments of the present invention and using methods according to embodiments of the present invention, respectively. FIG. 7a shows a white light image of a portion of a brain of a patient. A meshwork of capillaries and microcapillaries is observed penetrating underlying brain tissue. Thereby, the bright red capillaries 90 and 92 are arteries and the dark red capillaries 93 represent veins. Reference sign 91 denotes an aneurysm. FIG. 7b shows an image determined according to a method of the present invention showing a perfusion of blood cells in a region of the brain of the patient, wherein the region overlaps with the region of the brain illustrated in FIG. 7a. Values of the perfusion are represented by pseudo-color values (or grey values, respectively), comprising blue, yellow, red in increasing order. In particular, it is apparent that the capillaries 90, 92 and 93 exhibit a lower perfusion than adjacent brain tissue. A possible explanation is that a motion of blood cells in the capillaries 90, 92 and 93 is that fast (such as greater than 10 mm/s) that such a motion cannot be resolved any more by the detector used here.

Figure 8:
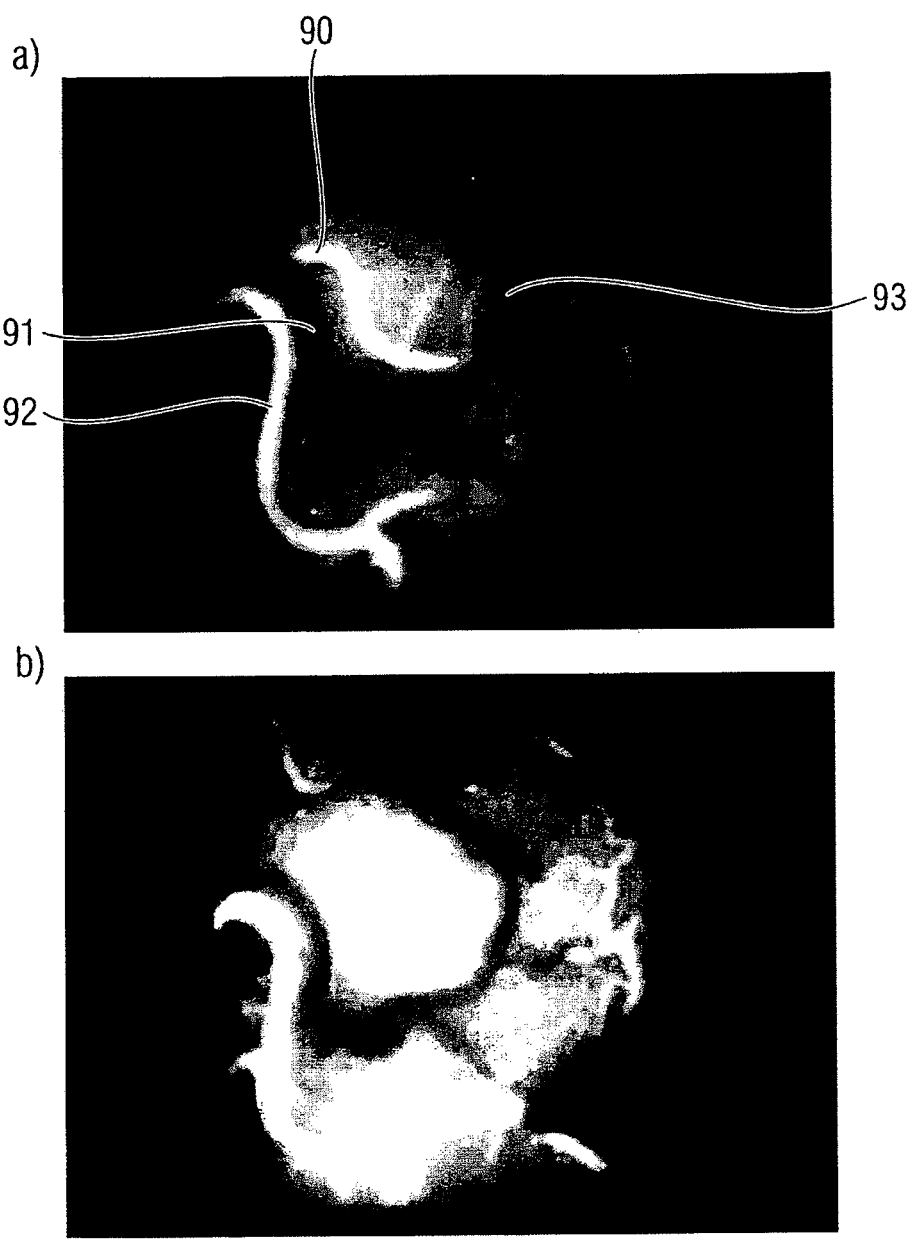
FIGS. 8a, 8b, 8c, 8d, 8e, and 8f show second images determined by detection of fluorescence of ICG, which were determined according to a method according to an embodiment of the present invention.
Figure 8:
Figure 8:
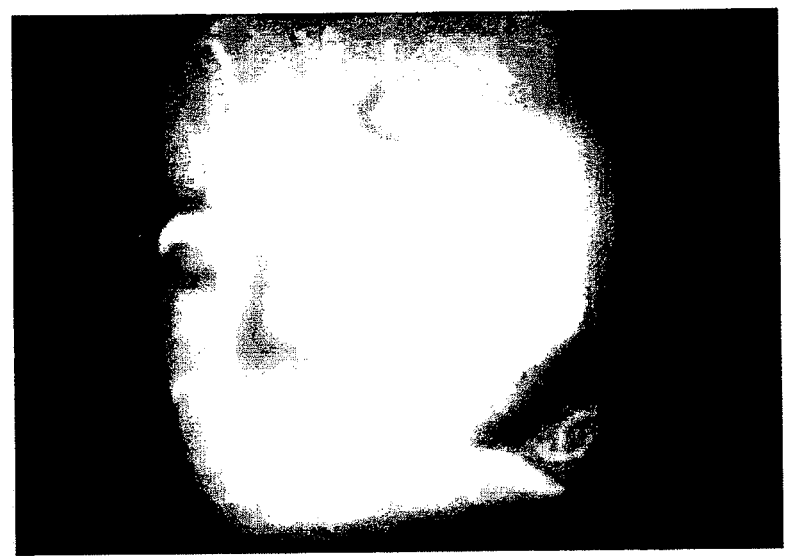
Figure 8:
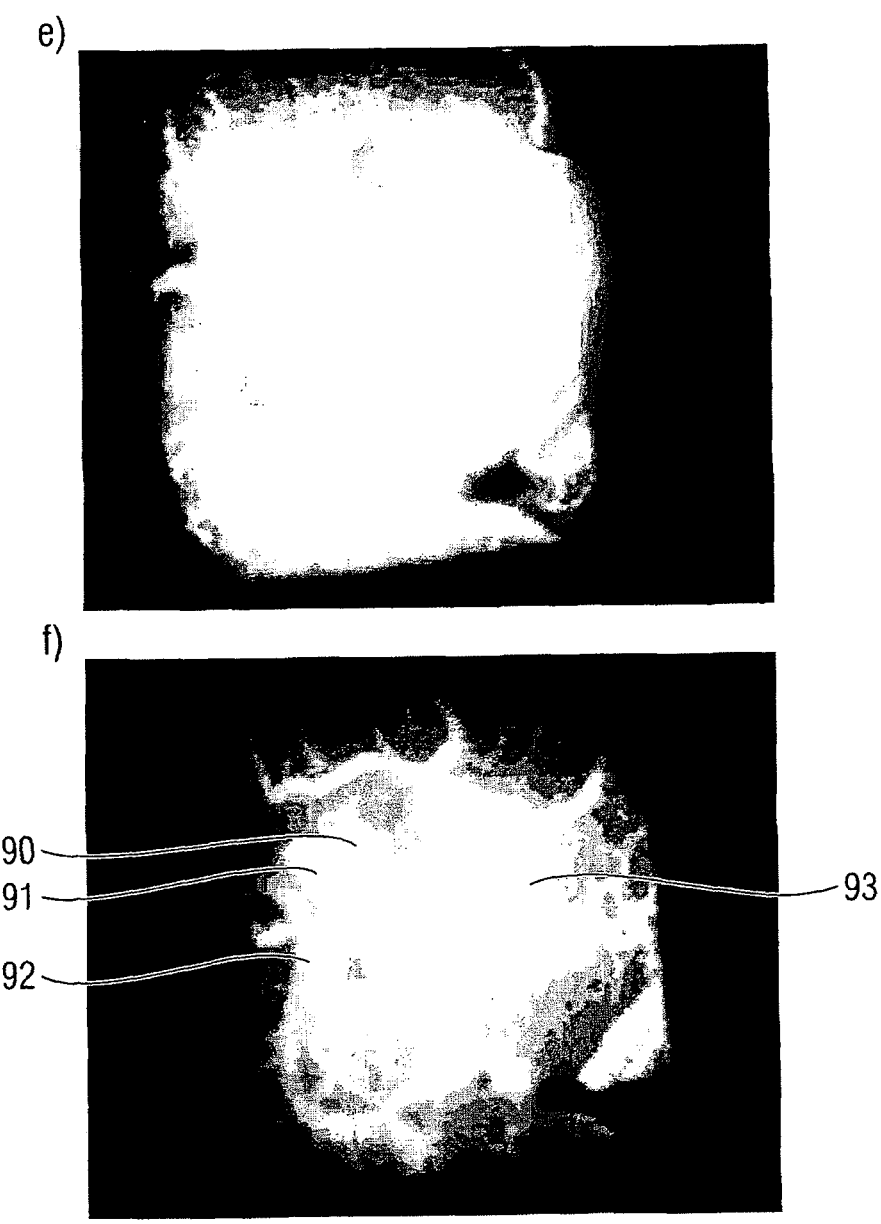

FIGS. 8a to 8f show images from a region of the brain overlapping with the regions illustrated in FIGS. 7a and 7b. The images shown in FIG. 8 are acquired by detection of fluorescence light of ICG by the second detector 70 illustrated in FIG. 6. The FIGS. 8a to 8f were recorded with a temporal interval of 0.5 s to 1 s and thus represent a temporal development of a fluorescence of ICG. Before the image 8a was recorded ICG was injected into the blood stream of the patient. After the injection of ICG initially (FIGS. 8a to 8d) an increasing intensity of fluorescence of ICG in the arteries, such as arteries 90 and 92, is observed. That means that ICG is supplied to the brain via the arteries. In contrast, in a region of the vein 93, practically no fluorescence of ICG is observed. The same holds for the aneurysm 91. FIG. 8e shows a condition in which the brain is maximally filled with ICG. Subsequently outflow of ICG from the examined region via veins occurs. This is shown in FIG. 8f. Thereby, vein 93 shows a high fluorescence intensity indicating that it guides blood. The same holds for the aneurysm 91 also indicating that the aneurysm is flown through by blood. A combination and evaluation of the images of the brain shown in the FIGS. 7 and 8 thus allows a detailed examination of the brain.

Figure 9:
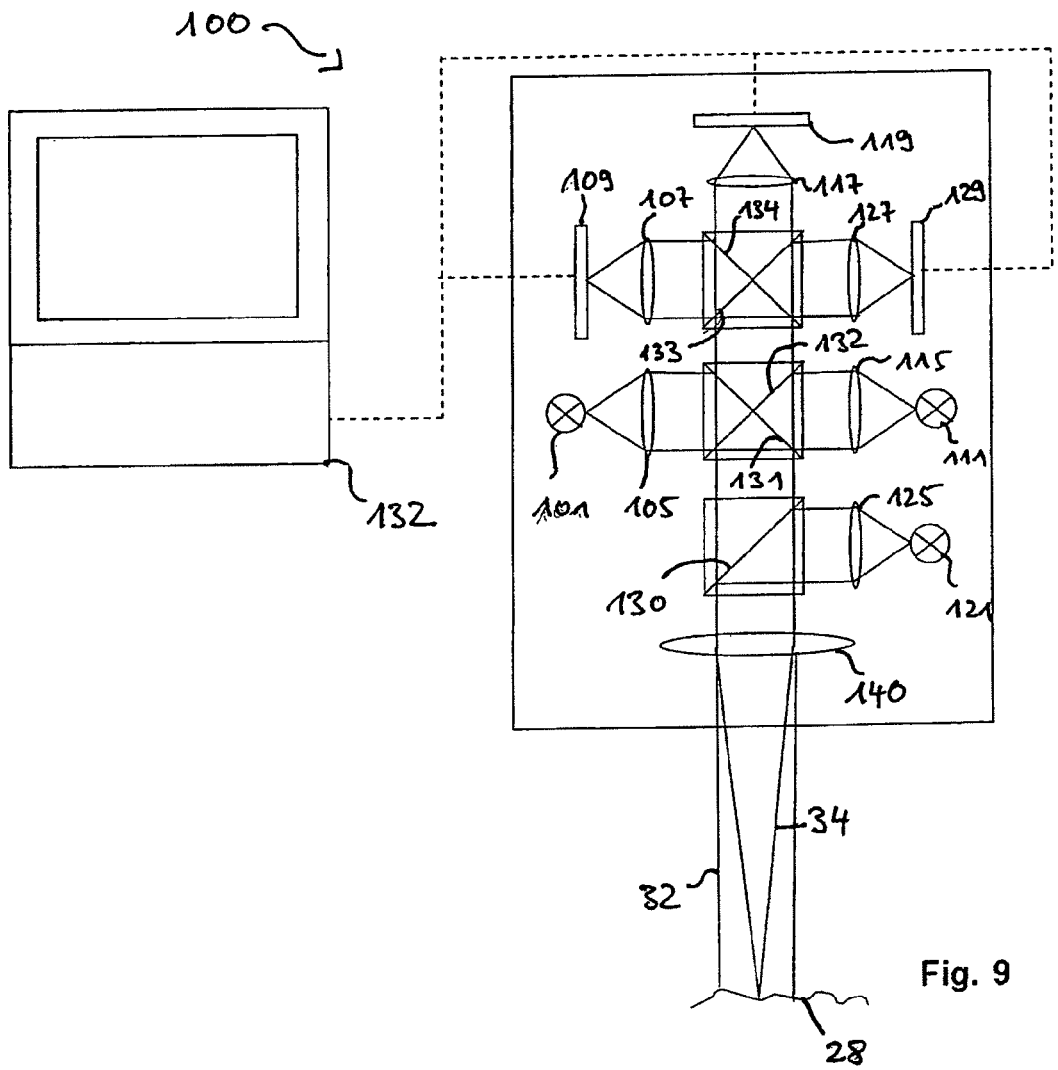
FIG. 9 illustrates a system for examining an object according to an embodiment of the present invention.

FIG. 9 shows a system 100 for examining an object according to an embodiment of the present invention. The system comprises a laser 101 for generating laser light which illuminates the object 28 after collimating it by a collimator 105 and reflection at the semi-transparent mirror 131, after traversal through the semi-transparent mirror 130 and traversal through the objective 140. The light of the laser 101 reflected from the object 28 is detected by the detector 109 after traversal through the semi-transparent mirror 130 through the two semi-transparent mirrors 131, 132 and reflection at the semi-transparent mirror 134 and traversal through camera optics 107. Light source 111 emits light comprising wavelengths in the range from 790 nm to 820 nm and is thus suited for excitation of fluorescence of ICG. Light generated by the light source 111 is collimated by the collimator 115, is reflected at the semi-transparent mirror 132, traverses through the semi-transparent mirror 130 and through the objective 140 to illuminate the object 28. There it excites fluorescence of ICG. The fluorescence light of ICG emanating from the object 28 is detected by the detector 119 after traversal through several semi-transparent mirrors and traversal through the camera optics 117. For this the detector 119 comprises a suitable filter to attenuate light having wavelengths outside a range from 820 nm to 850 nm from light detected by the detector 119 strongly in its intensity. The system 100 further comprises a white light source 121 for illuminating the object 28 with white light. The white light image of the object 28 is detected by the detector 129 after traversal through the objective and several semi-transparent mirrors and traversal through the camera optics 127. Sequences of images recorded by the detector 109 and images recorded by the detectors 119 and 129 are supplied to a monitor and evaluation unit 132. The monitor and evaluation unit 132 is adapted to derive perfusion data from the sequence of images received by the detector 109 and to display these perfusion data together with the white light image and the ICG fluorescence image and to process these further.

Figure 10:
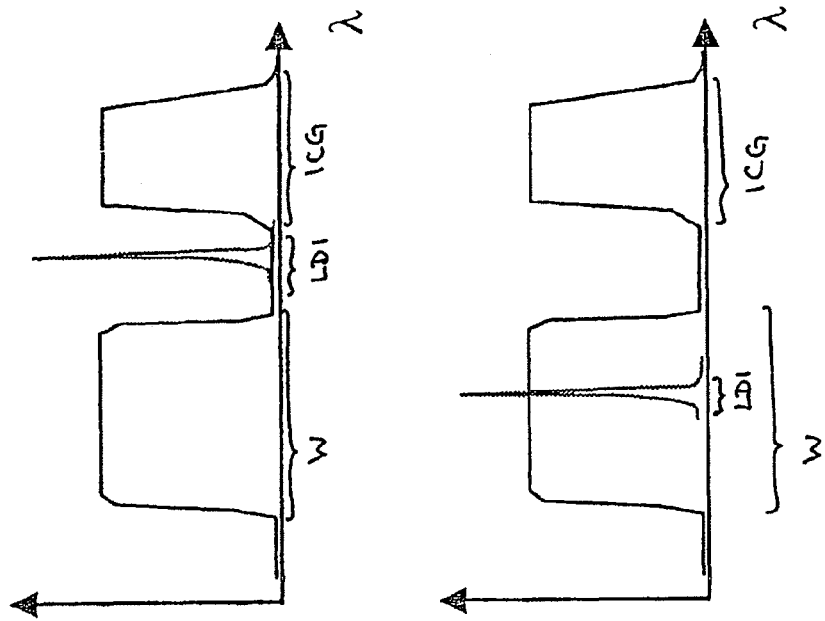
FIGS. 10a, 10b, 10c, and 10d illustrate a method according to an embodiment of the present invention for examining an object.
Figure 10:
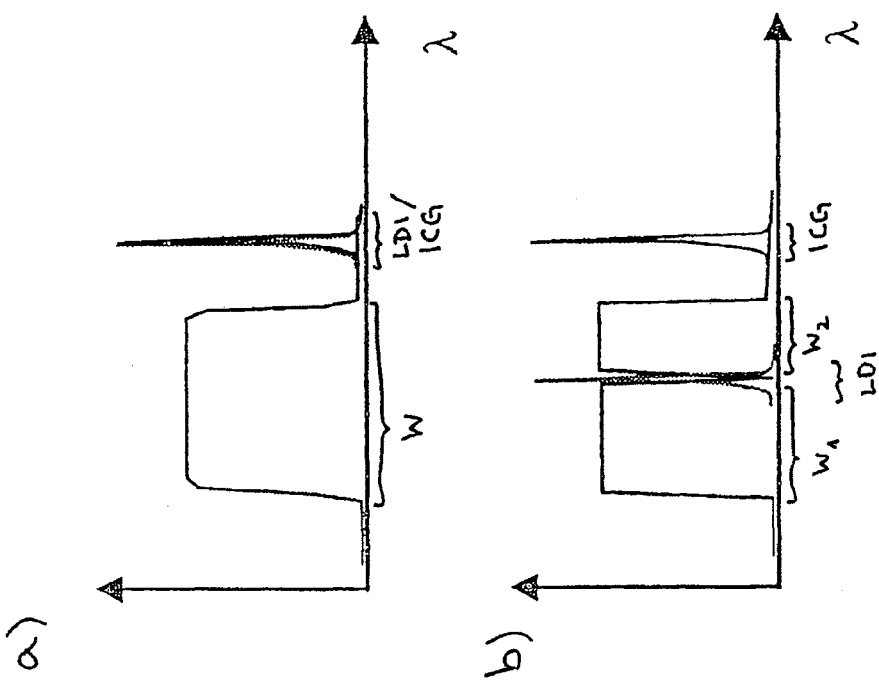
Figure 10:
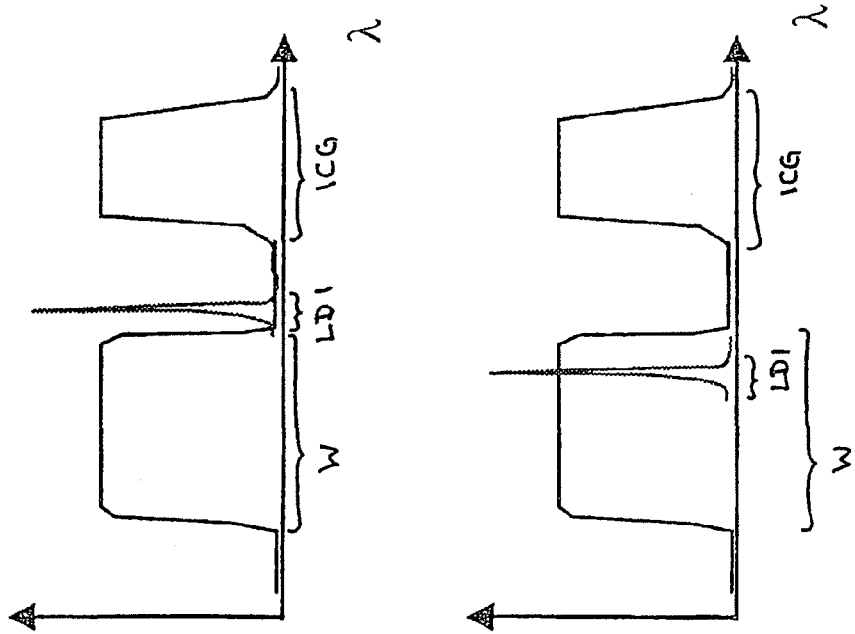
Figure 10:
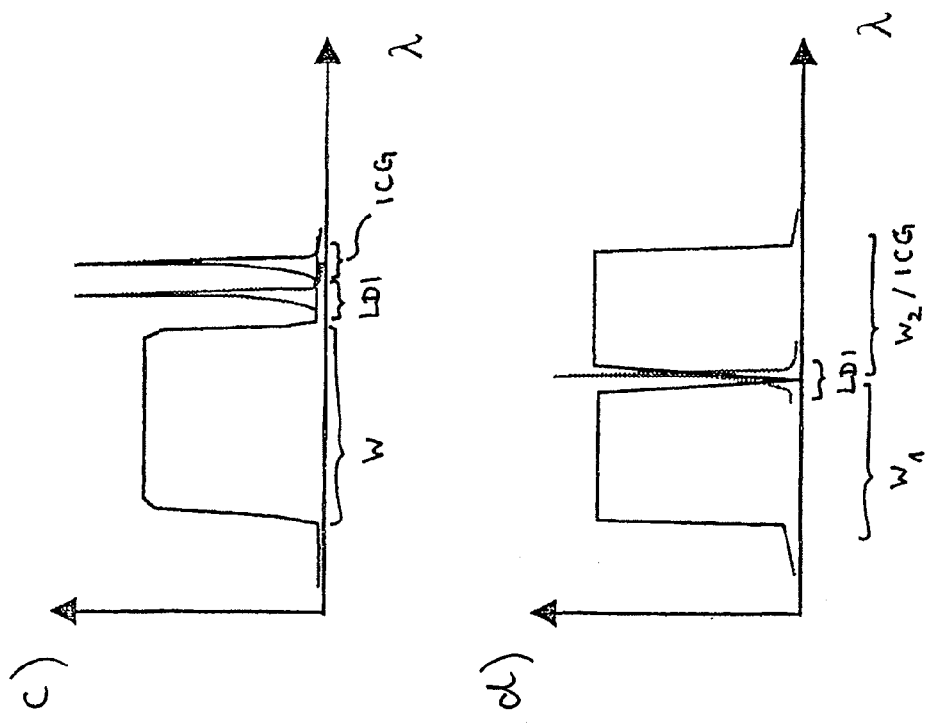

FIG. 10 shows methods according to embodiments of the present invention. FIGS. 10a to 10d show different illumination and detection scenarios according to embodiments of the present invention. In the FIGS. 10a to 10d on the left hand side an illumination strength in dependence of a wavelength is illustrated, respectively, and in the FIGS. 10a to 10d on the right hand side a detection sensitivity in dependence of the wavelength is illustrated, respectively. Depending on the embodiment, the illumination in different wavelength ranges may be performed by one or more light sources and the detection in different wavelength ranges may be performed by one or more detectors. With reference sign W in FIGS. 10a to 10d on the left hand side and the right hand side a white light illumination wavelength range and a white light detection wavelength range is denoted, respectively. With reference sign ICG in these Figures an illumination wavelength range for illumination with light suitable for excitation of fluorescence of ICG and a ICG detection wavelength range suited for detection of fluorescence of ICG is denoted, respectively. Reference sign LDI in these Figures denotes an illumination wavelength range and a detection wavelength range suited to detect laser Doppler signals from an illuminated sample which are suitable to obtain perfusion data about the object, respectively. The scenario illustrated in FIG. 10a may for example be realized using two light sources and three detectors. Hereby, the LDI illumination light is concurrently suited to excite fluorescence of ICG in the object. In embodiments, the LDI and/or ICG illumination light may be in a wavelength range overlapping or not overlapping with the illumination wavelength range of the white light illumination. An LDI detection wavelength range may in embodiments overlap with a detection wavelength range for white light detection or not. In the case of an overlap, the LDI detection signal may be separated from the white light detection signal by appropriate processing that may comprise an analysis of temporal changes of image values in a range above 1 kHz.

Summarized, embodiments of the present invention provide a system and a method for examining an object containing a fluid liquid, wherein the object is illuminated with measuring light and images are temporarily shortly subsequently recorded. The images are evaluated per pixel to determine perfusion data from a high frequency portion above 1 kHz and to determine further information about properties of the object from a low frequency portion below 100 Hz, such as a degree of oxygenation of hemoglobin, a concentration of hemoglobin or a concentration of ICG. This information determined by evaluation is displayed in a form of an image in superposition with a white light image of the object.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A method for examining an object containing a flowing liquid, the method comprising:
illuminating the object with measuring light and recording at least one sequence of first images ($I_k(i,j)$; k=1, ..., N) of the illuminated object, wherein an exposure time for each recording of an image of the at least one sequence of first images ($I_k(i,j)$; k=1, ..., N) is smaller than 1 ms;
evaluating, with an evaluation system, the at least one sequence of first images ($I_k(i,j)$; k=1, ..., N) by associating pixels (i,j) in the at least one sequence of first images ($I_k(i,j)$; k=1, ..., N) to which same locations (x,y) of the object are imaged with a first analysis image value, respectively, wherein the first analysis image value depends on fluctuations of image values ($I(t,i,j)$) of the pixels (i,j) in the at least one sequence of first images ($I_k(i,j)$; k=1, ..., N) in a frequency range above 1 kHz; and
evaluating, with the evaluation system, the at least one sequence of first images ($I_k(i,j)$; k=1, ..., N), by further associating pixels (i,j) in the at least one sequence of first images ($I_k(i,j)$; k=1, ..., N) to which same locations (x,y) of the object are imaged with a second analysis image value, respectively, wherein the second analysis image value depends on fluctuations of image values ($I(t,i,j)$) of the pixels (i,j) in the at least one sequence of first images ($I_k(i,j)$; k=1, ..., N) in a frequency range below 100 Hz, wherein the measuring light illuminating the object comprises wavelengths in a measuring light wavelength range from one of 605 nm to 630 nm, 560 nm to 580 nm, and 794 nm to 814 nm, and wherein the recording the at least one sequence of first images comprises detecting measuring light, wherein a ratio of an intensity of the detected measuring light having wavelengths outside the measuring light wavelength range from a total intensity of the detected measuring light amounts to less than 10%,
wherein the evaluation system comprises a processing system including a computer.

2. The method according to claim 1, wherein the recording the at least one sequence of first images ($I_k(i,j)$; k=1, ..., N) comprises recording temporally subsequent images with a temporal interval of smaller than 1 ms.

3. The method according to claim 1, wherein the measuring light has a coherence length corresponding at least to twice a penetration depth of the measuring light into the object.

4. The method according to claim 1, further comprising: illuminating the object with white light; and imaging and detecting the object illuminated with white light to determine a white light image of the object.

5. The method according to claim 1, wherein the first analysis image value associated with a pixel represents a value comprises one of a perfusion, a concentration, an average velocity, a measure for a velocity distribution, in particular a standard deviation of the velocity distribution, of particles moving relative to each other, in particular blood cells, and a combination of the same.

6. The method according to claim 1, further comprising at least one of displaying, in particular in superposition, and storing at least one of the first images, the first analysis image values, the second analysis image values, and the white light image for a plurality of pixels.

7. The method according to claim 1, further comprising repeating the recording the at least one sequence of first images ($I_k(i,j)$; k=1, ..., N) as temporal sequence and respective evaluating the repeatedly recorded at least one sequence of first images ($I_k(i,j)$; k=1, ..., N).

8. The method according to claim 1, wherein the object is part of a brain of a patient, in particular an aneurysm in the head of the patient.

9. The method according to claim 1, further comprising stimulating the patient.

10. The method according to claim 1, further comprising displaying a region of the object in dependence of a result of comparing of at least one of the first analysis image value, the second analysis image value, and an image value of at least one second image to preset threshold values for pixels to which the region of the object is imaged.

11. A method for examining an object containing a flowing liquid, the method comprising:
illuminating the object with measuring light and recording at least one sequence of first images ($I_k(i,j)$; k=1, ..., N) of the illuminated object, wherein an exposure time for each recording of an image of the at least one sequence of first images ($I_k(i,j)$; k=1, ..., N) is smaller than 1 ms;
evaluating, with an evaluation system, the at least one sequence of first images ($I_k(i,j)$; k=1, ..., N) by associating pixels (i,j) in the at least one sequence of first images ($I_k(i,j)$; k=1, ..., N) to which same locations (x,y) of the object are imaged with a first analysis image value, respectively, wherein the first analysis image value depends on fluctuations of image values ($I(t,i,j)$) of the pixels (i,j) in the at least one sequence of first images ($I_k(i,j)$; k=1, ..., N) in a frequency range above 1 kHz; and
evaluating, with the evaluation system, the at least one sequence of first images ($I_k(i,j)$; k=1, ..., N), by further associating pixels (i,j) in the at least one sequence of first images ($I_k(i,j)$; k=1, ..., N) to which same locations (x,y) of the object are imaged with a second analysis image value, respectively, wherein the second analysis image value depends on fluctuations of image values ($I(t,i,j)$) of the pixels (i,j) in the at least one sequence of first images ($I_k(i,j)$; k=1, ..., N) in a frequency range below 100 Hz, wherein the recording the at least one sequence of first images comprises detecting measuring light, wherein a ratio of an intensity of the detected measuring light having wavelengths greater than 850 nm and smaller than 500 nm from a total intensity of the detected measuring light amounts to less than 10%,
wherein the evaluation system comprises a processing system including a computer.

12. The method according to claim 11, wherein the measuring light has a coherence length corresponding at least to twice a penetration depth of the measuring light into the object.

13. The method according to claim 11, further comprising: illuminating the object with white light; and imaging and detecting the object illuminated with white light to determine a white light image of the object.

14. The method according to claim 11, wherein the first analysis image value associated with a pixel represents a value comprises one of a perfusion, a concentration, an average velocity, a measure for a velocity distribution, in particular a standard deviation of the velocity distribution, of particles moving relative to each other, in particular blood cells, and a combination of the same.

15. The method according to claim 11, further comprising at least one of displaying, in particular in superposition, and storing at least one of the first images, the first analysis image values, the second analysis image values, and the white light image for a plurality of pixels.

16. The method according to claim 11, further comprising repeating the recording the at least one sequence of first images ($I_k(i,j)$; k=1, ..., N) as temporal sequence and respective evaluating the repeatedly recorded at least one sequence of first images ($I_k(i,j)$; k=1, ..., N).

17. The method according to claim 11, wherein the object is part of a brain of a patient, in particular an aneurysm in the head of the patient.

18. The method according to claim 11, further comprising stimulating the patient.

19. The method according to claim 11, further comprising displaying a region of the object in dependence of a result of comparing of at least one of the first analysis image value, the second analysis image value, and an image value of at least one second image to preset threshold values for pixels to which the region of the object is imaged.

20. The method according to claim 11, wherein the recording the at least one sequence of first images ($I_k(i,j)$; k=1, ..., N) comprises recording temporally subsequent images with a temporal interval of smaller than 1 ms.

* * * * *